United States Patent [19]

Hussein et al.

[11] 4,445,892

[45] May 1, 1984

[54] DUAL BALLOON CATHETER DEVICE

[75] Inventors: Hany M. G. Hussein, Lindenhurst; Marvin P. Loeb, Chicago; Harvey S. Weiss, Buffalo Grove, all of Ill.

[73] Assignee: Laserscope, Inc., Arlington Heights, Ill.

[21] Appl. No.: 375,484

[22] Filed: May 6, 1982

[51] Int. Cl.³ .................... A61M 29/02; A61M 25/00
[52] U.S. Cl. .................................. 604/101; 128/4; 128/344
[58] Field of Search .............. 604/101, 102, 106, 97, 604/96; 128/4, 6, 325, 344, 303.1

[56] References Cited

U.S. PATENT DOCUMENTS

| | | | |
|---|---|---|---|
| 3,417,744 | 12/1968 | Mishkin et al. | 604/101 X |
| 3,818,902 | 6/1974 | Kinoshita et al. | 128/6 |
| 3,882,852 | 5/1975 | Sinnreich | 128/4 |
| 4,049,413 | 8/1977 | Ohshiro | 128/6 |
| 4,170,997 | 10/1979 | Pinnow et al. | 128/4 |
| 4,198,981 | 4/1980 | Sinnreich | 604/101 X |

Primary Examiner—Stephen C. Pellegrino

[57] ABSTRACT

A dual balloon catheter device is provided with two spaced and expandable balloons for occluding a segment of a blood vessel. The device also includes a first channel for flushing the occluded segment, an optic system for use in the segment, and a second channel for introducing fluid into the blood vessel distally of the device.

28 Claims, 7 Drawing Figures

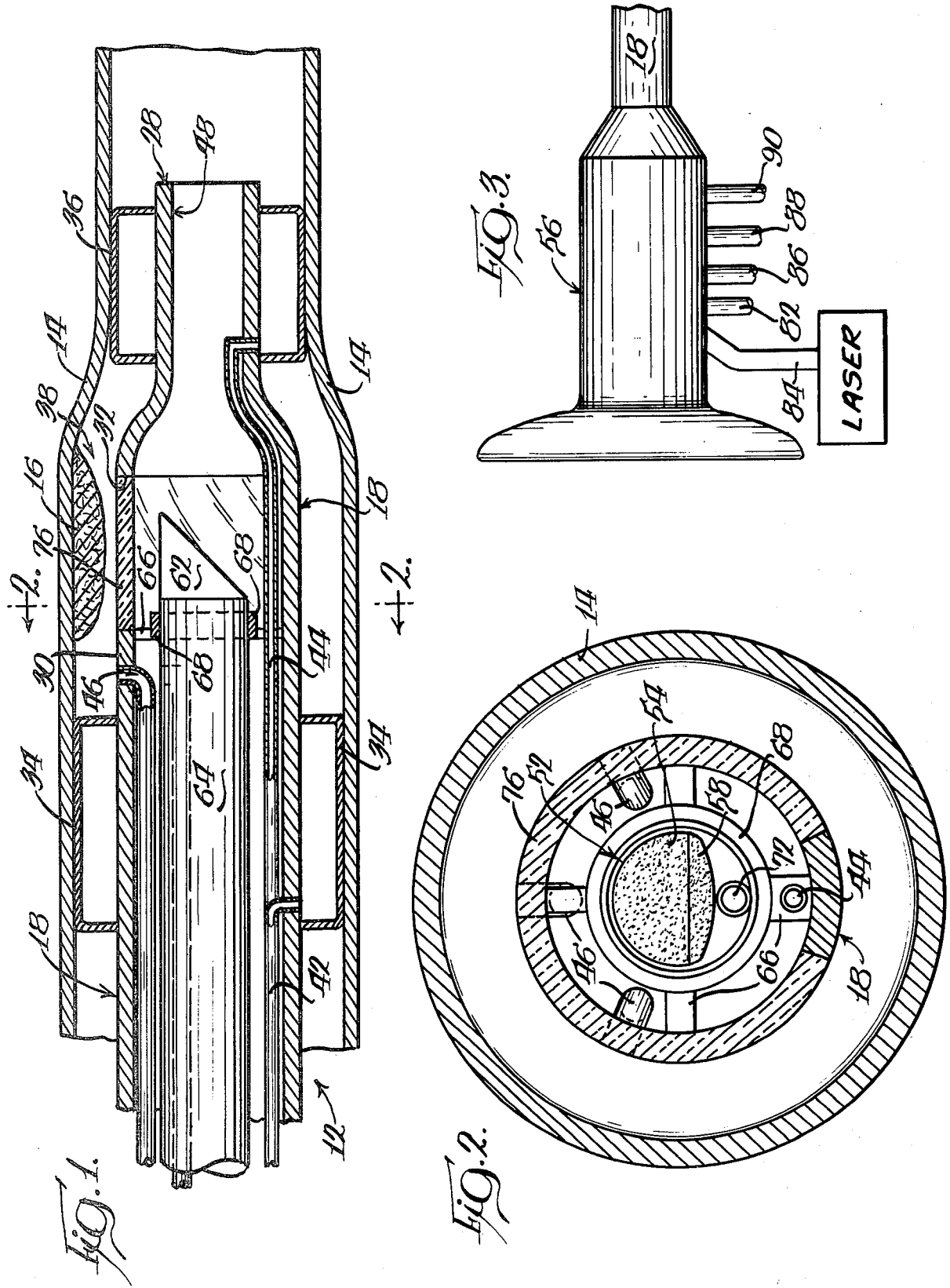

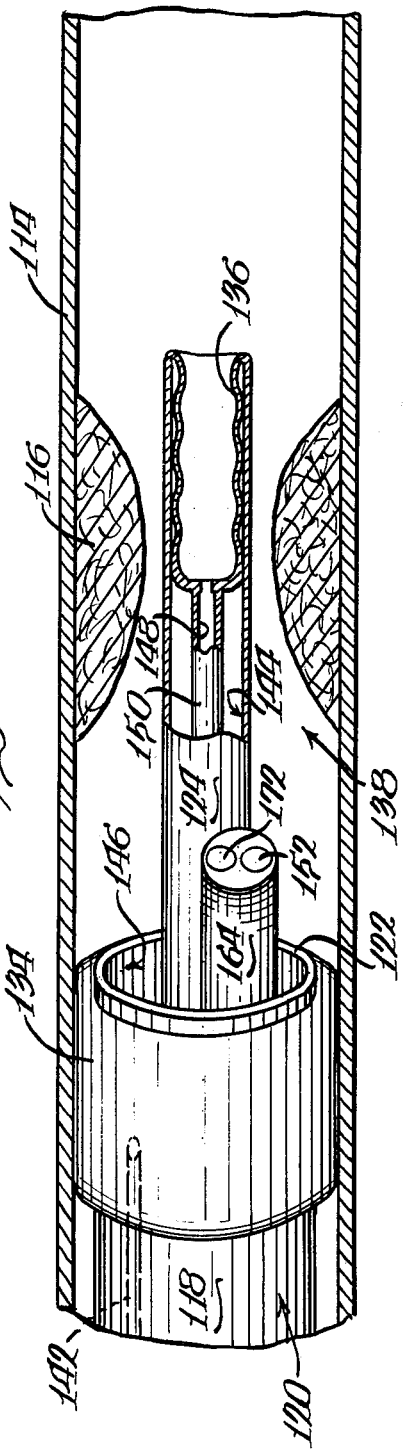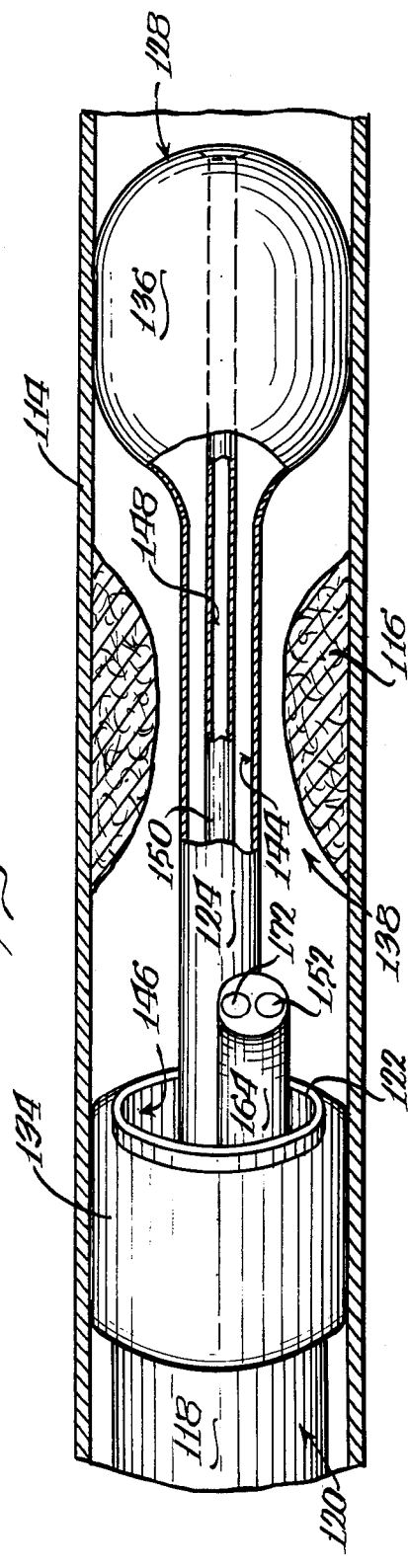

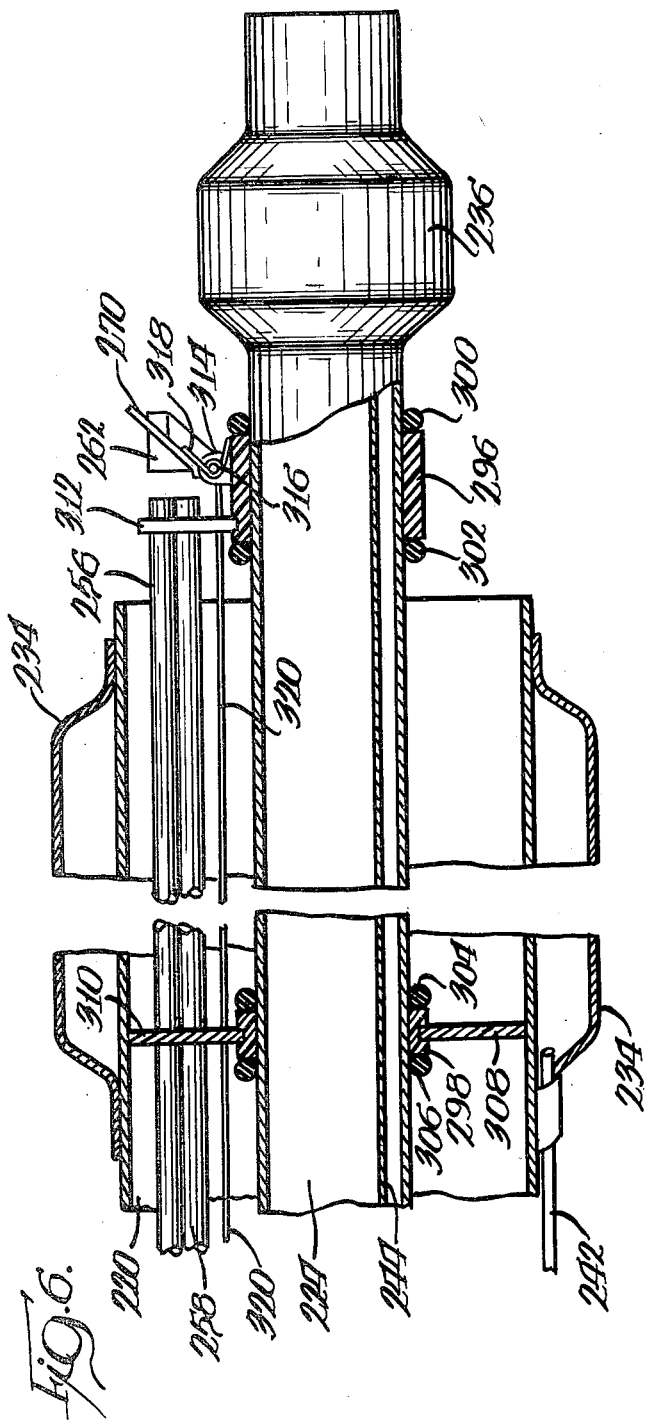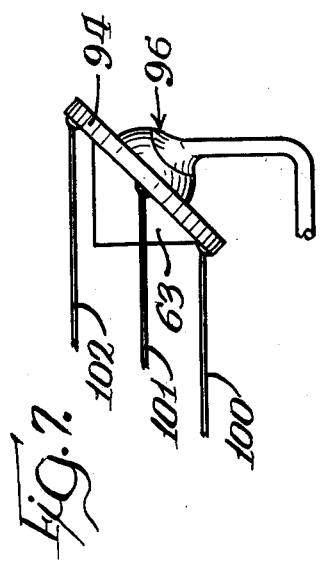

DUAL BALLOON CATHETER DEVICE

TECHNICAL FIELD

This invention relates to catheters for insertion into body lumens and in particular to catheters facilitating the use of optic systems within blood vessels, particularly arteries.

BACKGROUND OF THE INVENTION

Various fiber optic catheter devices have been proposed for use in blood vessels. These prior devices generally utilize an expandable balloon or other means to occlude the vessel while a clear fluid flushes downstream of the balloon to provide a clear operating region for the use of an optic system. This optic system can be a viewing system, a laser light transmitting system, or a combination of both.

Unfortunately, these prior devices have shortcomings. For example, none of the prior devices provide means for introducing an oxgyen bearing liquid downstream of the balloon and the clear operating region. However, if the supply of oxygen is interrupted for more than a few seconds, the tissue downstream of the balloon can suffer irreparable damage. Introducing a stream of flushing fluid such as an oxygen bearing liquid past the optic system is not always satisfactory because most oxygen-bearing liquids are opaque. Also, such a stream could wash debris away from the operating region before the debris could be collected and removed, e.g. with suction or flushing.

Even where a stream of flushing fluid is not present, the prior devices make no provision to prevent blood from diffusing into the flushing fluid in the operating region. Nor is there any provision for the sure recovery of any debris that may be liberated from the walls of the blood vessel. With these prior devices, any such debris can drift away from the device and be carried away by the flow of blood.

What is needed is a catheter device which avoids the deficiencies of the prior art and provides a clear and safe operating region within a blood vessel, while providing an oxygen bearing liquid to the tissue downstream of the device. It would also be desirable if such a device maintained a clear operating region and provided for expeditious recovery of any debris that may be generated. The present invention satisfies these desires.

SUMMARY OF THE INVENTION

The present invention is a dual balloon catheter device for insertion into a patient's blood vessel. This catheter device provides a clear but isolated operating region between the ballons positioned within the blood vessel, thereby facilitating the use of an optic system such as a viewing system or a laser, or both in conjunction therewith.

The catheter device generally includes a tubular structure carrying two spaced balloons which, when expanded, contact the blood vessel walls and occlude a segment of the vessel to define an operating region. The distal balloon usually is smaller than the proximal balloon, to permit entry into partially occluded blood vessels. A first fluid channel communicates with the occluded portion of the vessel to introduce a clear flushing fluid between the balloons and to remove any other fluid or debris therefrom. The optic system of the catheter device terminates between the two balloons to allow viewing, laser use, or both within the operating region.

The tubular structure also includes a second fluid channel for introducing a fluid such as an oxygen-bearing liquid distally of the second balloon. This provides oxygen to the tissues downstream of and thus beyond the operating region to prevent or reduce any ill effect to the tissue. Thus, a blood vessel can be occluded for a relatively longer period of time because oxygen is supplied through the second fluid channel to the tissue downstream.

The two balloons together with the walls of the blood vessel seal off the operating region from the rest of the vessel. After the sealed region has been flushed with a clear flushing fluid, it will remain clear and need not be repeatedly flushed or subjected to suction. In addition, where a tissue or obstruction removing means, such as a laser is used, any material liberated from the walls of the vessel will remain within the region to be removed by flushing suction. The liberated material will not drift away from the end of the catheter device, and the attendant threat of an embolism is therefore greatly reduced.

Numerous other advantages and features of the present invention will become readily apparent from the following detailed description of the invention, the drawings, the accompanying examples, and the appended claims.

BRIEF DESCRIPTION OF THE DRAWINGS

FIG. 1 is a side elevational view, partly in section, showing the distal portion of a catheter device embodying the present invention received within a blood vessel;

FIG. 2 is a cross-sectional view, taken generally along plane 2—2 of FIG. 1 showing the internal structure of the catheter device;

FIG. 3 is a side elevational view of the proximal portion of the catheter device;

FIG. 4 is a side elevational view, partially in section, showing the distal end of an alternative embodiment of the present invention received within a blood vessel;

FIG. 5 is a side elevational view, partly in section, of the catheter device of FIG. 4 showing a balloon expanded to contact the walls of the blood vessel;

FIG. 6 is a elevational view, partly in section and partly broken away to show interior detail, showing the distal portion of a catheter device illustrating yet another embodiment of the present invention; and FIG. 7 is an enlarged side elevational view illustrating an alternative mounting for a reflector means at the distal end of the optic system.

DESCRIPTION OF THE PREFERRED EMBODIMENTS

While this invention is susceptible of embodiment in many different forms, there are shown in the drawings and will be described in detail, preferred embodiments of the invention. It should be understood, however, that the present disclosure is to be considered as an exemplification of the principles of the invention and is not intended to limit the invention to the embodiments illustrated. In the Figures, legends having the same last two digits designate elements that perform a similar function in the depicted structures.

Referring to FIGS. 1-3, a dual balloon catheter device 12 is shown received within a blood vessel 14 having a constriction 16. The catheter device 12 generally includes an elongated outer tubular structure 18 having a distal end 28 and a wall 30 defining a window 32 spaced from the distal end. Window 32 can be an open aperture or can be provided with a clear protective pane, e.g. pane 76, as desired. A first expandable balloon 34 is carried peripherally about the tubular structure 18 adjacent to the window 32 but closer to the proximal end of device 12 than window 32. A second, smaller expandable balloon 36 is carried peripherally about the tubular structure between the distal end 28 and the window 32. Together with the blood vessel 14, the two balloons axially flank the window and define an occluded segment or operating region 38 within the vessel.

A first expansion fluid passageway 42 is provided in fluid communication with the first balloon 34 for expanding the first balloon, and a second expansion fluid passageway 44 is provided in fluid communication with the second balloon 36 for expanding the second balloon. A first flushing fluid channel 46 is a conduit mounted on and thus carried by the tubular structure 18. Channel 46 opens through the wall 30 between the first 34 and second 36 balloon.

A clear flushing fluid such as saline or carbon dioxide can be introduced through the flushing fluid channel 46 to provide substantially clear light transmission within the operating region 38. Preferably, a plurality, such as three, flushing fluid channels 46 are provided to direct a flow over the window 32. In use, the first balloon 34 can be expanded to seal a blood vessel so as to occlude blood flow. Clear flushing fluid can then be introduced through such channels 46 to displace the blood out of the operating region 38. The second balloon 36 can then be used to seal with the blood vessel to prevent blood from diffusing back into the operating region. Alternatively, both balloons can be expanded together and the operating region 38 cleared by introducing flushing fluid and/or suction through one or more flushing fluid channels 46.

The tubular structure 18 and the balloons 34 and 36, at least on their exterior surfaces, are of a material which is biocompatible for the time period during which the cathether device will be received within a blood vessel. Such materials include silicone rubber, natural rubber, polyvinyl chlorides, polyurethane, co-polyester polymers, thermoplastic rubbers, silicone-polycarbonate copolymers, polyethylene ethyl-vinyl-acetate copolymers, woven polyester fibers, or combinations of these. The catheter walls, especially the wall of the outer tubular structure, may be reinforced with stainless steel braid to enhance torque control. Radiopacity can be obtained by incorporating lead or barium salts into the catheter wall, if desired.

The balloons 34 and 36 are preferably elastomeric, with wall thickness of about 0.020 inches (about 0.5 mm). The tubular structure 18 is flexible and resilent along its length to allow it to be manipulated through blood vessels. The balloons 34 and 36 can be heat sealed, heat shrunk, or otherwise mounted onto the tubular structure 18 using techniques known in the art.

The tubular structure 18 also includes a conduit defining second fluid channel 48 which opens through the distal end 28 of the catheter device. This allows the introduction of an oxygen-bearing liquid such as blood or a liquid perfluorocarbon composition to supply oxygen to the tissues downstream of the catheter device. The blood vessel can be occluded without undue harm to downstream tissues. More involved procedures are therefore possible, and do not have to be performed under rushed conditions.

The oxygen-bearing liquid can be undiluted or diluted blood, or a liquid perfluorocarbon composition capable of carrying oxygen and other gases normally dissolved in blood. Such a composition can be a 10 to 20 percent emulsion of perfluorodecalin or perfluorotributylamine in a saline solution, for example. Preferably, the emulsion is prepared and oxygenated shortly before use. For the preparation and use of suitable perfluorocarbon emulsions reference is made to commonly-owned patent application entitled Method for Providing an Oxygen Bearing Liquid to a Blood Vessel for the Performance of a Medical Procedure, Ser. No. 349,718, filed on Feb. 18, 1982 by Marvin P. Loeb.

An optic system such as a viewing system 52 is carried by the tubular structure 18 and operably associated with the window 32. The optic system can be fixed on the tubular structure 18 or can be independently removable and replaceable by another optic system while the catheter device remains in place. When including a viewing system, the catheter device serves as an endoscopic device.

The viewing system 52 has an optical viewing conduit 54, coupling optics, some of which are carried within a handle 56 on the proximal end of the tubular structure, and means for emitting light from the terminal end of the viewing system such as a light transmitting bundle 58. The viewing conduit 54 can be any suitable structure such as a fiberoptic viewing bundle, a thin lens system, a rod lens system, or a graded index (GRIN) system, depending upon the flexibility requirements for the total assembly. The coupling optics can also include means for viewing through the window 32 such as a reflector means e.g. a mirror or prism 62. The operation of viewing conduits and coupling optics is well-known in the art and need not be described in further detail.

The optic system can also include a laser transmitting fiber in lieu of or in addition to the viewing system. The optic system is preferably located within a stem 64 which is rotatably carried within the tubular structure 18. The stem, made of a resilient material, can be rotated within the tubular structure 18 by mounts 66 and a rotation collar 68. The collar 68 can be provided with a surface coating to reduce friction and aid rotation, such as poly(tetrafluoroethylene). The window 32 extends over a substantial portion of the circumference of the tubular structure 18. This allows the optic system to be rotated with respect to the axis of the tube 18 while the balloons are expanded, thus a relatively large area of the vessel wall can be viewed or subjected to laser irradiation through the window 32.

Means for emitting laser irradiation through the window 32 are preferably provided with the viewing system. Laser irradiation can be directed through the opening by a laser transmitting fiber 72 located within the stem 64 and directed through the opening 32 by reflector means such as the prism 62. Alternatively, separate means such as a curved fiber can be provided to direct the laser irradiation through the window 32. Where a mirror is used as the reflector means, it preferably should have a coating to protect the mirror's reflectivity.

The mirror is preferably a coat of a dielectric or metallic film on the front surface of a flat piece of glass. Fused silicon and "Pyrex" glass substrates are preferred because of their high thermal shock resistance. A metallic coating can be aluminum, gold, silver, copper and rhodium. A film of silicon monoxide or magnesium fluoride (one half wavelength thickness) can be deposited over the metal for protection. A dielectric coating can be prepared by vacuum-deposition on a glass substrate of up to 30 quarter-wave layers of alternate magnesium fluoride and cerium dioxide films. The choice of coating depends on the angle and wavelength of the incident laser irradiation. The laser transmitting fiber 72 is preferably a single quartz glass fiber of about 100 to 200 micrometers in diameter having an inner core protected by an outer protective sheath. The end of the fiber 72 can also be provided with a replaceable quartz cover window, if desired, to further protect the fiber from damage.

The prism, mirror or fiber can also be moved by appropriate directing means such as one or more wires to enable a larger area of the vessel wall to be viewed or subjected to laser irradiation. Such an arrangement is illustrated in FIG. 7 where prism 63 is mounted on disk 94 provided with ball-and-socket joint 96. Four guide wires, such as guide wires 100, 101 and 102, are affixed about the periphery of disk 94 and are peripherally spaced about 90 degrees apart. The guide wires extend the full length of the catheter device and provide a convenient remote directing means for the reflector means used to guide the laser beam, the viewing light beam, or both.

Preferably, the window 32 is covered and sealed by a clear pane 76 to protect the optics within the tubular structure. The second fluid channel 48 is then defined by the interior of the tubular structure 18 and the pane 76. A separate tubule and its addition to the size of the device are then unnecessary as the remaining space within the tubular structure provides the second fluid channel. The window 32 and thus pane 76 preferably extend about a major portion of the circumference of the tubular structure 18 so that a large portion of the vessel wall can be viewed and subjected to laser irradiation as the stem 64 is rotated. When used with a viewing system, the pane 76 can be made of any suitable clear material such as glass, acrylic or poly(methyl methacrylate). When used with a laser system, the window should be of quartz glass and antireflection coated with a vacuum-deposited film of magnesium fluoride deposited in quarter-wave layers.

The handle 56 of the catheter device 12 is provided with a light source connection 82 operably associated with the light transmitting bundle 58 for connection to a bright light source such as a mercury arc lamp, a laser light conduit 84 operably associating the laser with the laser light transmitting fiber 72, a balloon connection 86 operably associated with the first and second fluid passageways 42 and 44 for connection to a fluid source, and fluid flow and suction connections 88 and 90 operably associated with the flushing fluid channel 46 and the flushing fluid channel 48 respectively, for connection to a fluid or vacuum source (not shown).

In use, the two balloons seal the operating region 138 so that the introduced flushing fluid remains clear. Any debris which may be liberated from the vessel walls as through laser use remains trapped within the operating region until suction is applied as through the fluid channel 46 or a separate suction channel. The second balloon 36, or both balloons, can then be contracted partially or in toto and the device moved to a new location or removed from the patient, as required.

An alternative design for the dual balloon catheter device is shown in FIGS. 4 and 5. As before, the catheter device includes a tubular structure 118 having a distal end 128. In this embodiment, the tubular structure 118 is constituted by an outer or first tube 120 and an independently positionable inner or second tube 124. The first tube 120 carries the first balloon 134 near the tube distal end 122 which end defines the window in this particular embodiment. The second tube 124 is slidably received within the first tube and can extend through the first tube beyond that tube's distal end. The second balloon 136 is carried adjacent the end of the second tube. As before, the two balloons occlude a portion of the blood vessel 114 to create the operating region 138 that encompasses constriction 116. The second tube 124 can be moved axially with respect to the first tube 120 to position the two balloons in a desired spatial relationship with respect to one another and thus create the desired sealed operating region 138 about the constriction that is to be removed or minimized.

The positioning of the second tube 124 within or outside the first tube 120 can be effected with the aid of a flexible-tip catheter guidewire that extends beyond distal end 122 of first tube 120. The guidewire is passed through channel 148 in tubule 150 and serves to guide the distal end of second tube 124 past the constriction 116. Alternatively, the second balloon 136 may be partially inflated and then flushing fluid dispensed through fluid channel 146 to flow-direct the second balloon 136-carrying end of second tube 124 further past the constriction 116 and to the desired position. Thereafter second balloon 136 can be inflated fully to seal off the operating state If second balloon 136 in its deflated state is carried on the outer surface of tube 124 insted of within tube 124, partial inflation of the balloon 136 for purposes of fluid-directed placement can be effected before the distal end of tube 124 passes through the region of constriction 116. Such partial inflation can also be utilized to close off in part fluid channel 146 during insertion of the catheter device. Subsequently, as the second tube 124 is advanced further along the blood vessel with respect to the outer sheath or first tube 120, fluid channel 146 is opened fully to permit a relatively larger volumetric flow rate of flushing fluid therethrough to guide and position second balloon 136.

Positioning of the catheter device embodying the present invention can be monitored by radioscopy or like techniques.

The viewing system 152 within the stem 164 is also carried within the first tube 120 and terminates either distally of the tube distal end 122 or sufficiently close to the distal end 122 within the first tube 120 such that the viewing system 152 is operably associated with the window defined by end 122 to permit illumination and viewing within the operating region 138. The stem 164 also preferably carries the laser light transmitting fiber 172 for emitting laser irradiation within the operating region 138 as at the constriction 116 on the walls of the blood vessel. The viewing system 152 and laser light transmitting fiber 172 preferably terminate between the two balloons. The stem 164 can be rotated and moved laterally with respect to the first tube 120 to position the viewing system 152 and laser light transmitting fiber 172 as desired. A mirror or prism, fixed or movable as described above, can also be used.

The space remaining within the first tube 120, and not occupied by the second tube 124 and the stem 164, defines the flushing fluid channel 146, which can be divided into two or more separate channels for flushing and suction, respectively if desired. This permits flushing and suction within the operating region 138. The second fluid channel 148 is defined by a tubule 150 which is a conduit that extends within the second tube 124 to the distal end of the second balloon 136. Passageway 144 defined by the second tube 124 and the tubule 150 provides a conduit for expanding the second balloon 136. As shown in FIG. 4, the second balloon 136 and tubule 150 can be retracted within the second tube when not in use. This provides for ease in positioning the catheter device and the second balloon as desired.

Alternatively, the second balloon 136 can be provided with a calibrated orifice or controlled leak at distal end 128 thus requiring a single passageway for both expanding the balloon and passing an oxygen-bearing liquid through an opening in the balloon into the blood vessel downstream of the device. In such a case tubule 150 is omitted and second tube 124 together with inner wall surface of balloon 136 define a common conduit that serves as passageway 144 as well as second fluid channel 148 which, in such an event, terminates in the aforementioned orifice.

The second balloon 136 can be mounted on the outer surface of or unitarily formed to be retractable within the second tube 124. For example, a length of tube can be heated until it becomes soft and then stretched lengthwise, causing the heated portion to form a constriction. Excess tubing can then be cut off at the constriction and a predetermined amount of gas pressure introduced into the tube. This inflates the heated portion into a baloon which is then cooled and joined to a tubule of relatively smaller diameter so as to provide a central passageway. The balloon is then a unitary part of the tube and there are no sealing joints which could break. The manufacturing technique for construction of a unitary tube-balloon structure are described in U.S. Pat. No. 4,254,774 to Boretos.

Yet another embodiment of the present invention is shown in FIG. 6. In this particular embodiment the dual balloon catheter device includes a flexible outer or first tube 220 provided with first expandable balloon 234 about the periphery of the tube 220. A flexible, albeit relatively more rigid, inner or second tube 224 is provided with second expandable balloon 236 near the distal end of the tube 224. An optic system rotatable about the longitudinal axis of the second or inner tube 224 is mounted thereon. The first balloon 234 is in fluid communication with a conduit defining the first fluid passageway 242. Likewise the second fluid passageway 244, defined by a conduit within inner tube 224, is for the expansion and collapse of the second balloon 236. The relative sizes of balloons 234 and 236 when expanded are adjustable and are selected as required to segregate a blood vessel region.

The optic system includes reflector means such as prism 262 as well as light-transmitting fiberoptic bundles 256 and 258. The optic system extends along inner tube 224 and is rotatably mounted thereon by means of spaced collars, such as end collar 296 and a plurality of spaced carrier collars such as carrier collar 298. The foregoing collars are longitudinally spaced along the inner tube 224 and are held in place by retainer means such as O-rings 300 and 302 for the end collar 296 and O-rings 304 and 306 for the carrier collar 298. The surfaces of the collars can include poly(tetrafluoroethylene) to reduce friction and aid rotational displacement, as well as axial displacement, if desired.

Elongated spacer members 308 and 310 are provided on the carrier collar 298 and extend radially outwardly, preferably touching the inside wall surface of outer tube 220. Spacer members 308 and 310 aid in the centering of the inner tube 224 within the outer tube 220. In addition, at least one spacer member on each carrier collar serves as a holder for the fiberoptic bundles 256 and 258. The distal end of the fiberoptic bundles 256 and 258 is held in place by the end holder 312 mounted on the end collar 296.

The prism 262 or like reflector means is positioned adjacent to the distal end of the fiberoptic bundles 256 and 258. The prism 262 is mounted on the base plate 270 which, in turn, is pivotally affixed to the end collar 296 via an apertured lug 314 and anchor pin 316. Spring 318 biases the prism base plate 270, and thus the prism 262, toward the distal ends of the fiberoptic bundles 256 and 258. Guide wire 320 is connected to the prism base plate 270 and extends rearwardly along inner tube 224 so that a pull on the guide wire 320 can position the prism 262 away from the distal ends of the fiberoptic bundles 256 and 258 at a desired angle.

The foregoing specification is intended as illustrative and is not to be taken as limiting. Still other variations within the spirit and scope of this invention are possible and will readily present themselves to those skilled in the art.

What is claimed is:

1. A catheter device for use within a blood vessel, comprising in operative association:
    (a) an elongated tubular structure having a distal end and defining a window spaced from the distal end;
    (b) first and second expandable balloons on the tubular structure and axially flanking the window;
    (c) a first fluid passageway defined by the structure and in fluid communication with the first balloon;
    (d) a second fluid passageway defined by the structure and in fluid communication with the second balloon;
    (e) a first fluid channel defined by the tubular structure and having an exit aperture through the tubular structure between the first and second balloons;
    (f) a second fluid channel defined by the tubular structure and providing a fluid passageway through the distal end; and
    (g) an optic system carried by the tubular structure and operably associated with the window, the optic system being rotatable with respect to at least a portion of the tubular structure.

2. The catheter device of claim 1 wherein the tubular structure includes a first tube having the first balloon mounted thereon and having a distal end defining the window, and a second tube extending through the first tube and beyond the distal end of the first tube and having the second balloon mounted thereon adjacent the outwardly projecting end of the second tube.

3. The catheter device of claim 1 wherein the optic system includes a viewing system.

4. The catheter device of claim 1 wherein the optic system includes means for emitting laser irradiation.

5. The catheter device of claim 1 wherein the optic system includes a viewing system mounted on a stem within the tubular structure and rotatable with respect to the tubular structure.

6. The catheter device of claim 1 wherein the optic system includes a laser emitting means mounted on a stem within the tubular structure and rotatable with respect to the tubular structure.

7. The catheter device of claim 1 further including a substantially clear pane extending over and sealing the window.

8. The catheter device of claim 7 wherein the second fluid channel is defined by the tubular structure and the pane.

9. The catheter device of claim 1 wherein the optic system includes a prism positioned in proximity of and operably associated with the window.

10. The catheter device of claim 9 including directing means for moving the prism with respect to the window.

11. The catheter device of claim 1 wherein the optic system includes a mirror operably associated with the window.

12. The catheter device of claim 11 including directing means for moving the mirror with respect to the window.

13. The catheter device of claim 1 wherein the second balloon is smaller in diameter than the first balloon.

14. A catheter device for introduction within a blood vessel, comprising in operative combination:
(a) an elongated tubular structure having a wall and a distal end;
(b) a first expandable balloon peripherally about the tubular structure and spaced from the distal end;
(c) a first fluid passageway defined by the catheter device in fluid communication with the first balloon;
(d) a second expandable balloon peripherally about the tubular structure, spaced from the first balloon and adjacent the distal end
(e) a portion of the tubular structure wall between the first and second balloon that is substantially clear and defines a window;
(f) a first fluid channel defined by the tubular structure and having an opening through the wall between the first and second balloon;
(g) a second fluid channel defined by the tubular structure and having an opening through the distal end;
(h) a stem rotatably mounted within the tubular structure; and
(i) an optic system on the stem and terminating adjacent the window;
whereby the catheter device can be received within the blood vessel and a clear flushing fluid introduced through the first fluid channel and another fluid can be introduced through the second fluid channel into the blood vessel.

15. The catheter device of claim 14 wherein the optic system includes a viewing system.

16. The catheter device of claim 14 wherein the optic system includes a laser light transmitting means.

17. The catheter device of claim 14 wherein the second balloon is smaller in diameter than the first balloon.

18. A catheter device for introduction within a blood vessel, comprising in operative combination:
(a) a first elongated tube having a distal end;
(b) a first expandable balloon peripherally about the first tube;
(c) a first fluid passageway defined by the catheter device and in fluid communication with the first balloon;
(d) a second elongated tube within the first tube positioned so that one end of the second tube is extendable beyond the distal end of the first tube;
(e) a second expandable balloon peripherally about the second tube adjacent to the one end;
(f) a second fluid passageway defined by the catheter device and in fluid communication with the second balloon;
(g) an optic system in the first tube, terminating between the first and second balloons and movable with respect to the first tube;
(h) a first fluid channel defined by a conduit in the first tube for introducing and removing fluid between the first and second balloons; and
(i) a second fluid channel defined by a conduit in the second tube for introducing fluid distally of the second balloon;
whereby the distal portion of the catheter device can be received within the blood vessel, the balloons expanded and the region between the balloons flushed and another fluid introduced into the blood vessel through the second fluid channel.

19. The catheter device of claim 18 wherein the optic system includes a viewing system.

20. The catheter device of claim 18 wherein the optic system includes a laser emitting means.

21. The catheter device of claim 18 wherein the second balloon is retractable into the second tube.

22. The catheter device of claim 18 wherein the second balloon is smaller in diameter than the first balloon.

23. An endoscopic device for viewing within a blood vessel, comprising in operative combination:
(a) a first elongated tube having a distal end;
(b) a first expandable balloon mounted peripherally about the first tube near the distal end;
(c) a first fluid passageway defined by a conduit within the first tube and in fluid communication with the first balloon;
(d) a second elongated tube extendable through the first tube so that one end of the second tube projects beyond the distal end of the first tube;
(e) a second expandable balloon peripherally about the second tube on the end portion of the second tube that can project beyond the distal end of the first tube;
(f) a second fluid passageway defined by a conduit in the second tube and in fluid communication with the second balloon;
(g) a viewing system within the first tube and terminating between the distal end of the first tube and the second balloon and rotatable about the axis of the second tube;
(h) a laser light transmitting fiber within the first tube and terminating between the distal end of the first tube and the second balloon;
(i) a first fluid channel defined between the first tube and the second tube and providing a through opening at the distal end of the first tube; and
(j) a second fluid channel defined by a conduit in the second tube and providing a through opening distally of the second balloon;
whereby the distal portion of the endoscopic device can be received within the blood vessel and fluid introduced into and removed from the space defined by the balloons and the blood vessel through the first fluid channel to provide a clear view through the viewing system.

24. The endoscopic device of claim 23 wherein the second balloon is smaller in diameter than the first balloon.

25. The endoscopic device of claim 23 wherein the optic system includes reflector means carried by the second tube for viewing and laser use away from the longitudinal axis of the tube.

26. The endoscopic device of claim 25 including at least one control wire extending through the first tube for moving the reflector means.

27. The endoscopic device of claim 25 wherein the reflector means is a prism.

28. The endoscopic device of claim 23 wherein the second tube together with the second balloon define the second fluid passageway and the second fluid channel.

* * * * *